United States Patent
Lee et al.

(10) Patent No.: US 11,000,355 B2
(45) Date of Patent: May 11, 2021

(54) TEST DEVICE AND TEST METHOD USING THE SAME

(71) Applicant: IUCF-HYU(INDUSTRY-UNIVERSITY COOPERATION FOUNDATION HANYANG UNIVERSITY), Seoul (KR)

(72) Inventors: Sang-Kyung Lee, Seoul (KR); Irfan Ullah, Seoul (KR); Kunho Chung, Seoul (KR); Sangah Lee, Groton, MA (US); Priti Kumar, Hamden, CT (US)

(73) Assignee: IUCF-HYU (INDUSTRY-UNIVERSITY COOPERATION FOUNDATION HANYANG UNIVERSITY), Seoul (KR)

(*) Notice: Subject to any disclaimer, the term of this patent is extended or adjusted under 35 U.S.C. 154(b) by 239 days.

(21) Appl. No.: 16/061,298

(22) PCT Filed: Dec. 6, 2016

(86) PCT No.: PCT/KR2016/014220
§ 371 (c)(1),
(2) Date: Jun. 11, 2018

(87) PCT Pub. No.: WO2017/099446
PCT Pub. Date: Jun. 15, 2017

(65) Prior Publication Data
US 2018/0360583 A1    Dec. 20, 2018

(30) Foreign Application Priority Data
Dec. 11, 2015 (KR) .................. 10-2015-0177443

(51) Int. Cl.
*A61D 3/00* (2006.01)
*A61D 7/00* (2006.01)
(Continued)

(52) U.S. Cl.
CPC ................ *A61D 3/00* (2013.01); *A61D 7/00* (2013.01); *A61D 7/04* (2013.01); *A61K 49/0008* (2013.01)

(58) Field of Classification Search
CPC ...... A61D 3/00; A61D 2003/003; A61D 5/00; A61B 5/0555
(Continued)

(56) References Cited

U.S. PATENT DOCUMENTS 2,982,248 A * 5/1961 Hosko, Jr. ................ A61D 3/00
                                                         119/729
3,466,090 A * 9/1969 Posey ....................... A61G 5/10
                                                         297/484
(Continued)

FOREIGN PATENT DOCUMENTS

JP    6-127998    8/1997
KR    10-1280350    7/2013

OTHER PUBLICATIONS

International Search Report for PCT/KR2016/014220 dated Mar. 15, 2017, 2 pages, in Korean language.
(Continued)

*Primary Examiner* — Yvonne R Abbott-Lewis
(74) *Attorney, Agent, or Firm* — Sughrue Mion, PLLC

(57) ABSTRACT

A test device is disclosed. The test device includes a supporter providing a seating surface for an experimental animal, and a chair formed on the supporter and configured to induce a drug inhalation posture in which a head of the experimental animal is directed downward. Thus, a mecca position may be induced by a simple operation of seating an unconscious experimental animal on the chair. As a result, nose-to-brain drug delivery may be performed.

9 Claims, 7 Drawing Sheets

(51) Int. Cl.
*A61D 7/04* (2006.01)
*A61K 49/00* (2006.01)

(58) Field of Classification Search
USPC .................................................. 119/417–421
See application file for complete search history.

(56) References Cited

U.S. PATENT DOCUMENTS

| | | | | |
|---|---|---|---|---|
| 3,612,605 | A * | 10/1971 | Posey, Jr. ............... | A61F 5/3792 |
| | | | | 297/484 |
| 4,120,266 | A * | 10/1978 | Oloff ....................... | A61D 3/00 |
| | | | | 119/755 |
| 4,213,424 | A * | 7/1980 | Hosch .................. | A01K 1/0613 |
| | | | | 119/728 |
| 4,254,767 | A * | 3/1981 | Mixon, Jr. ............... | A61D 3/00 |
| | | | | 128/869 |
| 4,620,540 | A * | 11/1986 | Goodale ................. | A61D 3/00 |
| | | | | 128/869 |
| 5,005,526 | A * | 4/1991 | Parker .................. | A01K 1/0272 |
| | | | | 119/751 |
| 5,676,426 | A * | 10/1997 | Herring ................. | A47D 15/006 |
| | | | | 297/484 |
| 5,816,256 | A * | 10/1998 | Kissinger ............... | A01K 1/031 |
| | | | | 128/897 |
| 5,890,769 | A * | 4/1999 | Fairbanks ............ | A47D 15/006 |
| | | | | 297/467 |
| 6,959,962 | B2 * | 11/2005 | Dixon .................... | A61G 7/065 |
| | | | | 297/195.11 |
| 7,806,088 | B2 * | 10/2010 | Osada .................... | A01K 1/031 |
| | | | | 119/712 |
| 8,365,739 | B1 * | 2/2013 | Jones ................... | A61G 13/122 |
| | | | | 128/845 |
| 2004/0070253 | A1 * | 4/2004 | Murphy ................. | A61B 50/33 |
| | | | | 297/423.11 |
| 2014/0379224 | A1 * | 12/2014 | Hyde ................... | A61G 5/1056 |
| | | | | 701/49 |

OTHER PUBLICATIONS

International Search Report for PCT/KR2016/014220 dated Mar. 15, 2017, 2 pages, English translation from WIPO.

* cited by examiner

[Fig. 1]
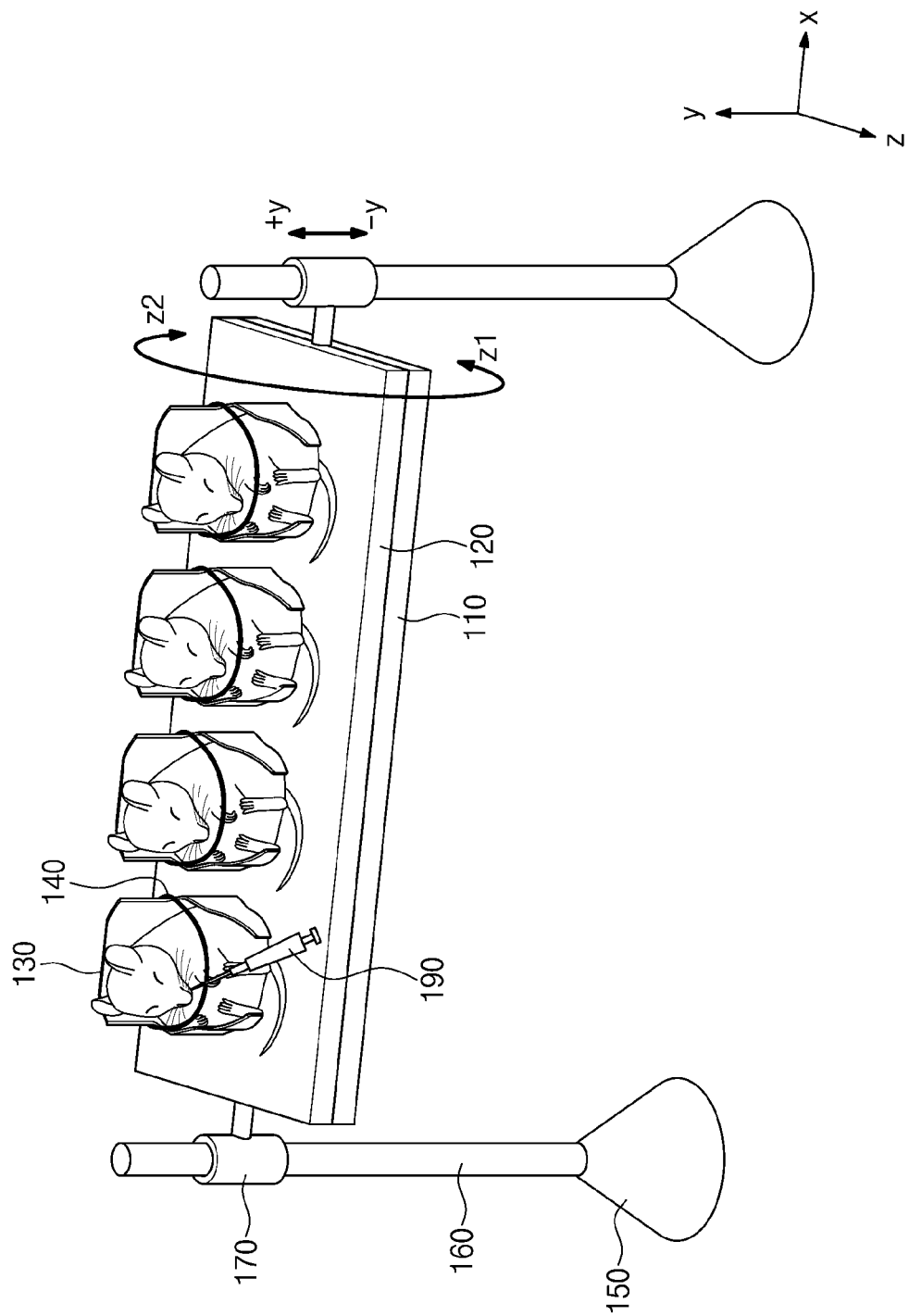

[Fig. 2]
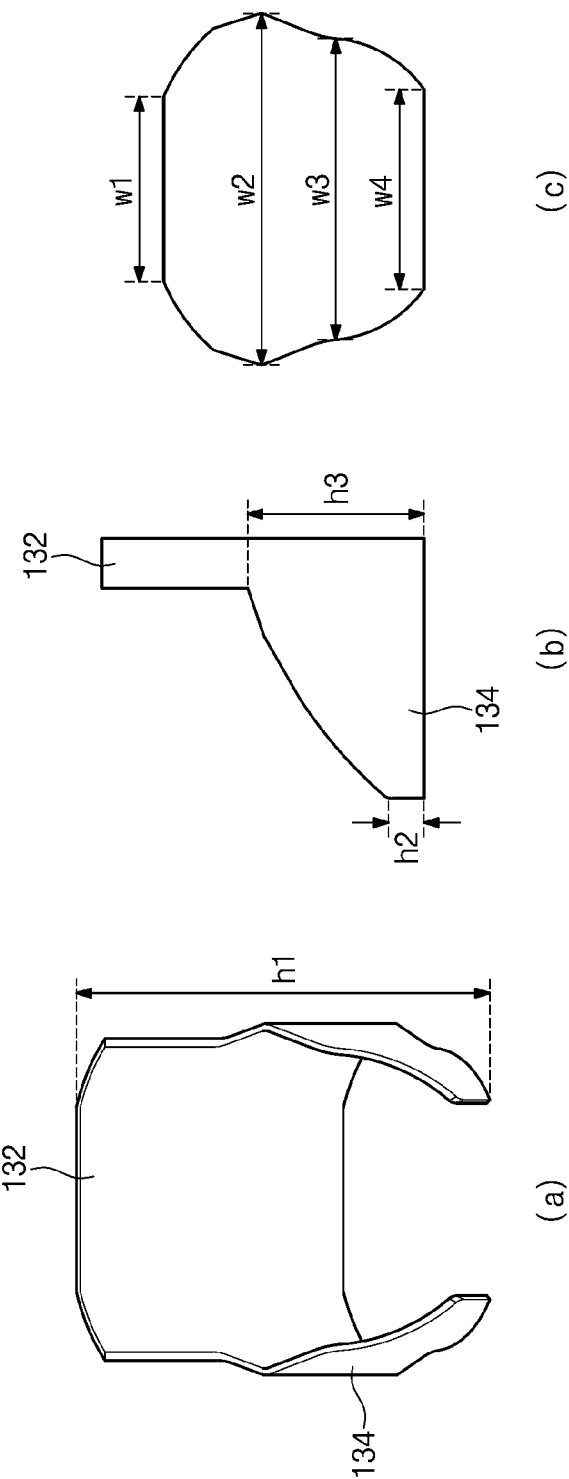

[Fig. 3]
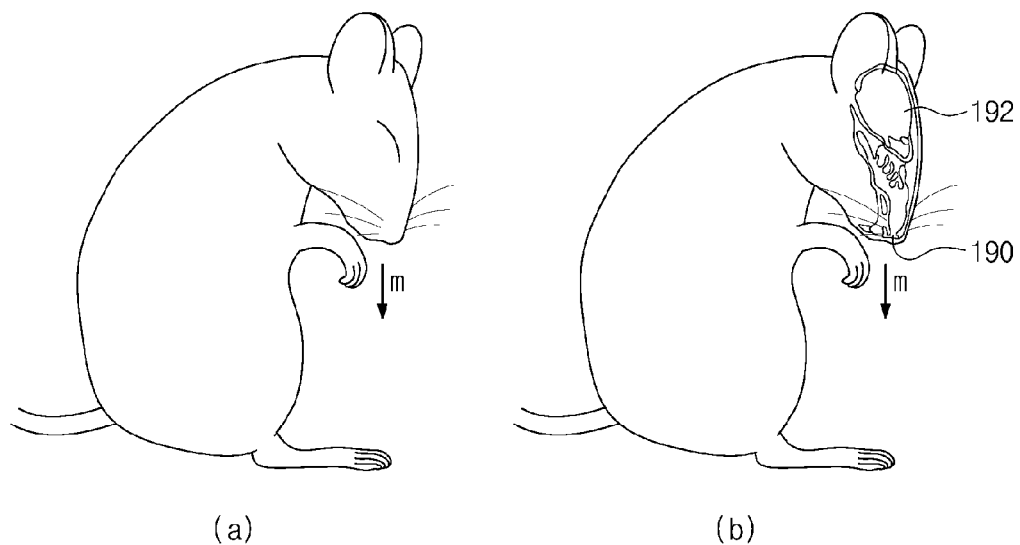
(a)　　　　　　　　　(b)
[Fig. 4]
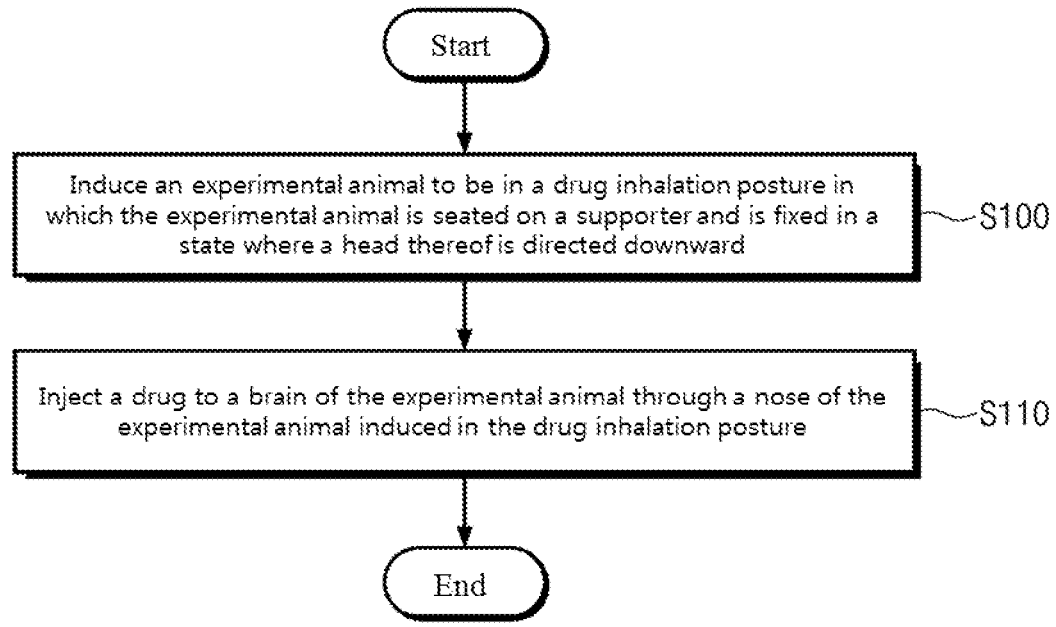

[Fig. 5]
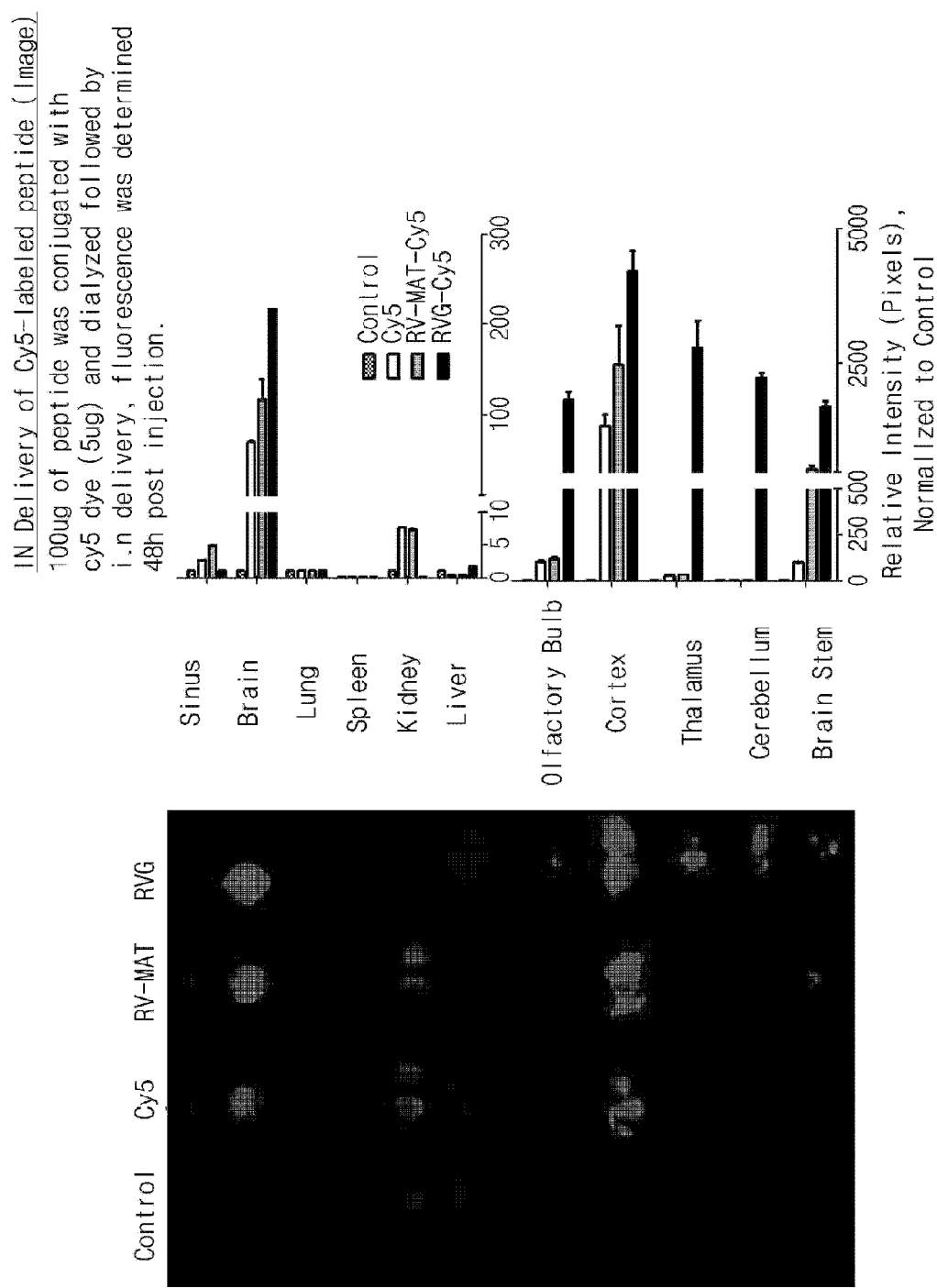

[Fig. 6]
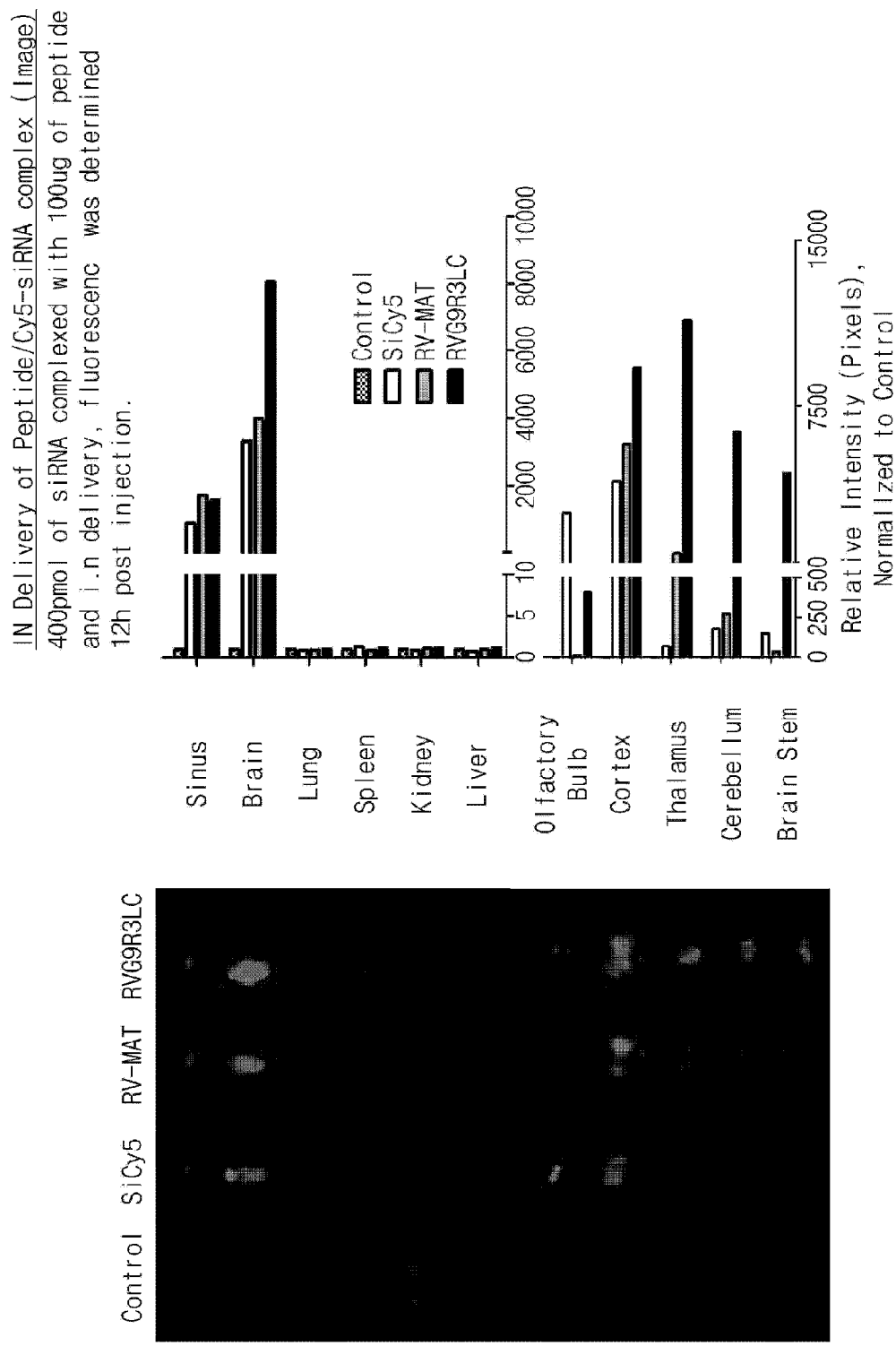

[Fig. 7]
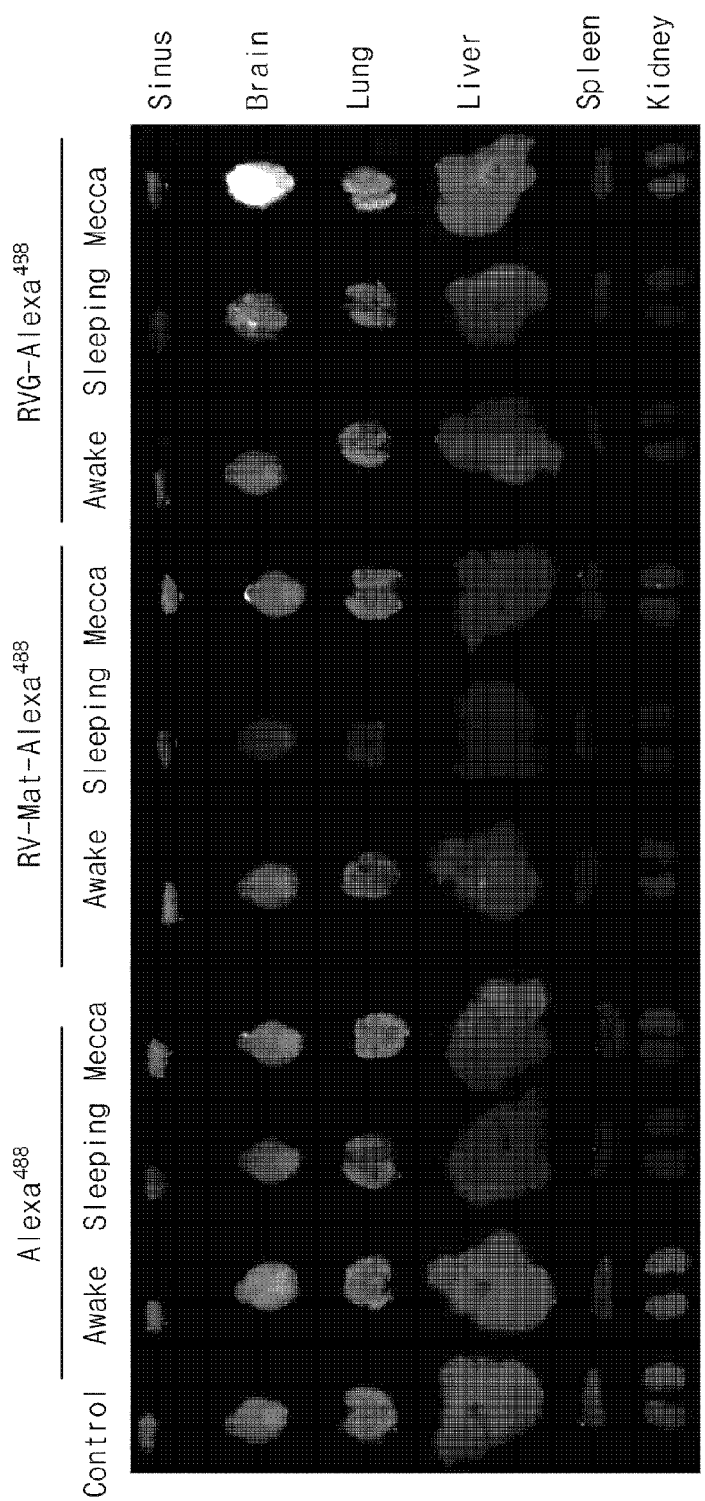

[Fig. 8]
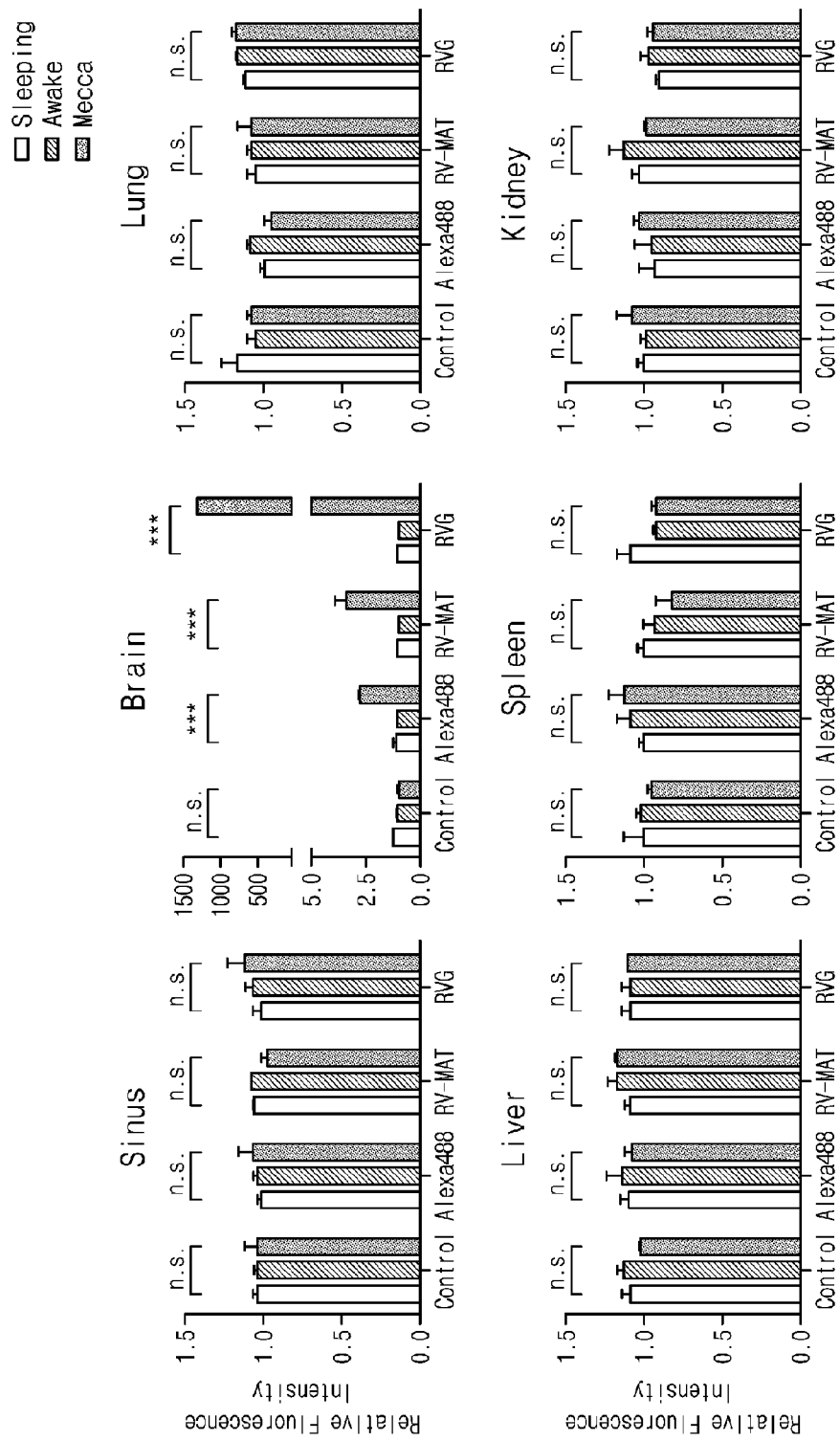

TEST DEVICE AND TEST METHOD USING THE SAME

CROSS-REFERENCE TO RELATED APPLICATION

This application is a continuation of pending International Application No. PCT/KR2016/014220, which was filed on Dec. 6, 2016 and claims priority to Korean Patent Application No. 10-2015-0177443, filed on Dec. 11, 2015, in the Korean Intellectual Property Office, the disclosures of which are hereby incorporated by reference in their entireties.

BACKGROUND

1. Field

The present disclosure herein relates to a test device and a test method using the same, and more particularly, to a test device capable of performing nose-to-brain drug delivery by inducing a drug inhalation posture in which the head of an experimental animal is directed downward, and a test method using the test device.

2. Description of the Related Art

Devices for testing animals (hereinafter, referred to as 'test devices') may mean devices which predict potential responses, which may occur in the human body, by observing pharmacological responses of experimental animals to which drugs are administered or by observing responses of experimental animals to which external stimuli (e.g., electricity and/or disease-causing germs) are applied.

The test devices may include a metabolic test device, an environment test device, a cigarette smoke generator, a behavior test device, and a gas test device. For example, the metabolic test device may mean a device which separately collects feces and urine according to feed and water supplied to experimental animals. The environment test device may mean a test device for checking environments such as powder (collected powder) and/or drugs. The cigarette smoke generator may be a device for evaluating the hazard of the cigarette, and the behavior test device may be a device for evaluating behavior characteristics through an elevator and/or a running machine. The gas test device may be a device for performing a test in a gas environment such as hydrogen, nitrogen and/or carbon dioxide.

Meanwhile, recently, techniques for directly delivering drugs to a brain through a nose (nose-to-brain) have been actively studied. In particular, since the nose is a region in which olfactory bulb neurons recognizing smells and trigeminal neurons moving facial muscles are exposed to the outside, it may be a spot through which a drug is effectively injected to the brain. For example, recently, hormone such as neuropeptide has been injected through a nose to help treatment of neurological disorders or obesity.

However, due to difficulty of paths toward the brain through the olfactory bulb neurons and the trigeminal neurons in the nose, it is not easy to inject a drug into the brain through the nose. Thus, a degree of the injection of the drug into the brain through the nose may be varied depending on a skill level of an operator.

Thus, it is required to develop a test device for delivering a drug from a nose to a brain.

SUMMARY

The present disclosure may provide a test device capable of performing nose-to-brain drug delivery, and a test method using the same.

The present disclosure may also provide a test device capable of effectively performing nose-to-brain drug delivery regardless of a skill level of an operator, and a test method using the same.

The present disclosure may further provide a test device which has a simple structure and is easily operated, and a test method using the same.

The present disclosure may further provide a test device capable of improving a survival rate of an experimental animal, and a test method using the same.

In an aspect, a test device may include a supporter providing a seating surface for an experimental animal, and a chair formed on the supporter and configured to induce a drug inhalation posture in which a head of the experimental animal is directed downward.

In an embodiment, a warm pad may be formed on the supporter, and the warm pad may be configured to maintain a body temperature of the experimental animal.

In an embodiment, a bottom of the chair may be opened, and the warm pad may be exposed through the chair.

In an embodiment, the chair may include a belt connected to both sides of the chair and configured to fix the experimental animal.

In an embodiment, the chair may surround a left side, a right side and a back side of the experimental animal and the belt may surround and fix a front side of the experimental animal.

In an embodiment, the supporter may extend in a longitudinal direction and the chair may be provided in plurality in the longitudinal direction.

In an embodiment, the supporter may extend in a longitudinal direction and may be configured to rotate on an axis parallel to the longitudinal direction.

In an embodiment, the test device may further include holders disposed at both sides of the supporter to support the supporter. The supporter may be vertically movable in a height direction of the holders.

In an aspect, a test method may include inducing an experimental animal to be in a drug inhalation posture in which the experimental animal is seated on a supporter and is fixed in a state where a head thereof is directed downward, and injecting a drug to a brain of the experimental animal through a nose of the experimental animal induced in the drug inhalation posture.

In an embodiment, the test method may further include maintaining a body temperature of the experimental animal to which the drug is injected.

BRIEF DESCRIPTION OF THE DRAWINGS

FIG. 1 is a view illustrating a test device according to an embodiment of the inventive concepts.

FIG. 2 illustrates a chair of a test device according to an embodiment of the inventive concepts.

FIG. 3 illustrates side views of an experimental animal according to an embodiment of the inventive concepts.

FIG. 4 is a flowchart illustrating a test method according to an embodiment of the inventive concepts.

FIGS. 5 and 6 show test results of nose-to-brain drug delivery of a test device according to an embodiment of the inventive concepts.

FIGS. 7 and 8 show test results of nose-to-brain drug delivery according to drug injection through a non-mecca position and drug injection through a mecca position according to an embodiment of the inventive concepts.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

FIG. 1 is a view illustrating a test device according to an embodiment of the inventive concepts.

A test device 100 according to an embodiment of the inventive concepts may be a device for testing various experimental animals such as a mouse, a rat, a guinea pig, a hamster, and a rabbit. Hereinafter, the embodiment in which the experimental animal is the mouse will be described for the purpose of ease and convenience in explanation. However, technical features of the inventive concepts may also be applied to other experimental animals.

The test device 100 according to an embodiment of the inventive concepts may be used when the experimental animal is unconscious. In the present specification, the term 'unconsciousness' may mean a consciousness disorder state in which there are no sensory perception and memory of an experimental animal and there are no responses of the experimental animal to external environmental stimuli.

Referring to FIG. 1, the test device 100 according to an embodiment of the inventive concepts may include a supporter 110 and a chair 130 provided on the supporter 110. In addition, the test device 100 according to an embodiment of the inventive concepts may include at least one of a warm pad 120 provided on the supporter 110, a supporting part 150, a holder 160, or a joint 170. Hereinafter, each of the components will be described in detail.

In an embodiment, the supporter 110 may provide a support surface on which the experimental animal may be seated. For example, the supporter 110 may be formed of a material capable of supporting a weight of the experimental animal, e.g., plastic, wood, or metal. The supporter 110 may extend in a transverse direction (e.g., an x-axis direction) and may have a length in the x-axis direction, which is capable of seating at least one experimental animal. In an embodiment, four experimental animals may be seated on the supporter 110, as illustrated in FIG. 1. In addition, the supporter 110 may extend in a depth direction (e.g., a z-axis direction) and may have a length in the z-axis direction, which is capable of seating at least one experimental animal. In an embodiment, one experimental animal may be seated in the z-axis direction, as illustrated in FIG. 1.

The warm pad 120 may be formed on the supporter 110 to maintain a body temperature of the experimental animal. For example, the warm pad 120 may maintain the body temperature of the experimental animal in a range of about 36 degrees Celsius to about 37 degrees Celsius. The experimental animal may be seated on the warm pad 120 to maintain the body temperature of the experimental animal. The warm pad 120 may include a component capable of controlling a temperature. For example, the warm pad 120 may include at least one of a metal resistance heater or a thermoelectric element.

The warm pad 120 may be controlled by at least one of various methods. For example, the warm pad 120 may be turned on/off by an operator. Alternatively, when the experimental animal is seated on the warm pad 120, the warm pad 120 may sense a weight of the experimental animal through a weight sensor (not shown) formed on the warm pad 120, and thus a state of the warm pad 120 may be automatically changed from an off state into an on state. In other words, since the warm pad 120 is automatically controlled depending on whether the experimental animal is seated thereon or not, convenience of an operator may be improved.

The warm pad 120 may be formed as a single body corresponding to a plurality of experimental animals or may be locally formed to correspond to an individual experimental animal. For example, when the warm pad 120 is locally formed to correspond to the individual experimental animal, only an area on which the experimental animal is seated may be selectively turned on/off.

The chair 130 may be provided on the supporter 110. In more detail, the chair 130 may be provided on the warm pad 120. The chair 130 may support the experimental animal, and thus the chair 130 may be formed of a material harmless to the experimental animal, for example, plastic, wood, or metal.

The chair 130 may induce a drug inhalation posture (i.e., a mecca position) in which a head of the experimental animal is directed downward. At this time, the experimental animal for forming the mecca position may be in an unconscious state for convenience of operation.

According to an embodiment, the chair 120 may be formed of a material harmless to the experimental animal, for example, plastic, wood, or metal. In an embodiment, the chair 130 may be formed of a flexible material.

In particular, the drug inhalation posture in which the head of the experimental animal is directed downward (e.g., faces the ground) may be an effective posture for nose-to-brain drug injection. In other words, generally, drug injection through a nose-to-brain path may be blocked by a blood-brain barrier. However, when the experimental animal takes the mecca position in which the head is directed downward, the nose-to-brain drug injection may be possible.

The drug inhalation posture in which the head of the experimental animal is directed downward will be described in more detail with reference to FIG. 3.

FIG. 3 illustrates side views of an experimental animal according to an embodiment of the inventive concepts. A side view (a) of FIG. 3 illustrates the experimental animal seated on the chair, and a side view (b) of FIG. 3 illustrates an anatomical cross section of the experimental animal of the side view (a) of FIG. 3.

Referring to the side view (a) of FIG. 3, when an unconscious experimental animal is seated on the chair 130 according to an embodiment of the inventive concepts, a heavy head of the experimental animal is naturally dropped toward the ground. Thus, the mecca position in which an entrance of the nose of the experimental animal is directed to the ground may be taken (see a direction 'm').

Referring to the side view (b) of FIG. 3, the entrance 191 of the nose is directed to the ground by a simple operation of seating the unconscious experimental animal on the chair 130 (see a direction 'm'). Thus, when a drug is injected through the entrance 191 of the nose, the drug may be delivered to a brain 192 without being affected by a blood-brain barrier.

According to the embodiment of the inventive concepts, for the nose-to-brain drug delivery, the drug inhalation posture in which the head is directed downward may be induced by the simple operation of seating the unconscious experimental animal on the chair 130. Thus, simplicity and convenience of the operation may be improved, and the drug inhalation posture may be easily induced due to the simplicity of the operation regardless of a skill level of an operator.

Next, the chair according to an embodiment of the inventive concepts will be described with reference to FIG. 2. FIG. 2 illustrates a chair of a test device according to an embodiment of the inventive concepts. In more detail, a view (a) of FIG. 2 is a front view of the chair, a view (b) of FIG. 2 is a side view of the chair, and a view (c) of FIG. 2 is a plan view of the chair.

Referring to the views (a) and (b) of FIG. 2, the chair 130 may include at least one of a back support portion 132 and a side support portion 134. The back support portion 132 may be a component for supporting the waist of the experimental animal. The side support portion 134 may be a component for supporting a leg part of the experimental animal and may extend from each of both ends of the back support portion 132.

The chair 130 may be designed to conform to a body shape of the mouse corresponding to the experimental animal. For example, a height h1 of the back support portion 132 of the chair 130 may be 5 cm. The side support portion 134 of the chair 130 may include a first portion corresponding to a hip part of the experimental animal and a second portion corresponding to an end of a leg of the experimental animal. The first portion of the side support portion 134 may have a height h3 of 2 cm, and the second portion of the side support portion 134 may have a height h2 of 1.4 cm.

Meanwhile, according to an embodiment, a bottom of the chair 130 may have an opened shape. Since the bottom of the chair 130 is opened, the experimental animal may be seated directly on the warm pad 120. Thus, efficiency of maintaining the body temperature of the experimental animal may be improved. Referring to the view (c) of FIG. 2 which illustrates the opened shape of the chair 130, the bottom opening of the chair 130 may have a width w1 of 2.5 cm, a width w2 of 4.1 cm, a width w3 of 3.7 cm, and a width w4 of 2.3 cm to correspond to a bottom of the hips of the mouse being the experimental animal.

As a result, even though the experimental animal is in an unconscious state, the experimental animal may be seated in a shape surrounded by the chair 130 and thus may stably take the mecca position.

Referring again to FIG. 1, the test device 100 according to an embodiment of the inventive concepts may further include a belt 140.

The belt 140 may be a component for fixing the front of the experimental animal seated on the chair 130 and may include a strap which extends from both ends of the chair 130 to tighten the front of the experimental animal.

The supporting part 150 may provide an interface with a bottom, and the holder 160 may extend from the supporting part 150 in a height direction (i.e., a y-axis direction). The holder 160 may be formed of a solid material (e.g., a material including iron) to stably transfer a weight of the supporter 110 to the supporting part 150. In addition, the holder 160 may be provided at each of both ends of the supporter 110 and may be coupled to the supporter 110 via the joint 170.

The joint 170 may fix the supporter 110 and may be configured such that the supporter 110 is movable in the height direction (i.e., the y-axis direction) if necessary. For example, the supporter 110 may be lifted in a +y-axis direction of the holder 160 or be lowered in a −y-axis direction of the holder 160 in a state in which the coupling between the supporter 110 and the joint 170 is released. In addition, the supporter 110 may be coupled again to the joint 170 at an adjusted location. Since the joint 170 is configured such that the supporter 110 is vertically movable along the holder 160, a working environment suitable to each of operators may be realized even though heights of the operators are different from each other.

In addition, the joint 170 may also be configured to rotate the supporter 110 on an x-axis with respect to the holder 160. For example, the joint 170 may rotate the supporter 110 in a z1 direction and may rotate the supporter 110 in a z2 direction. In an embodiment, the supporter 110 may be rotated in the z2 direction to easily seat the experimental animal. After seating the experimental animal, the supporter 110 may be rotated in the z1 direction to induce the mecca position of the experimental animal. As a result, since the joint 170 is configured to rotate the supporter 110 on the x-axis, the convenience of the operation may be further improved.

On the other hand, according to an embodiment, a drug may be injected into the nose of the experimental animal by a drug injector 190. For example, the drug injector 190 may be driven by a spray drug injection method, a drug injection method using tube injection, or a drug injection method using a syringe. However, embodiments of the inventive concepts are not limited thereto. The drug injector 190 may be driven by another method capable of delivering a drug through the nose. When the drug injector 190 includes a syringe-type injection device, an discharge portion corresponding to a syringe needle may be inserted in the nose of the experimental animal, and then, a discharge pressure applying portion corresponding to a piston of the syringe may be operated to administer a liquid drug to the nose. At this time, the shape of the injection device is not limited to a shape of a general syringe. When the drug injector 190 includes a spray-type injection device, like the syringe-type injection device, a discharge portion may be located at a nostril (i.e., the entrance of the nose) or in the nose, and then, spraying pressure may be applied to administer a drug into the nose in the form of spray. When the drug injector 190 includes a tube-type injection device, a discharge portion (e.g., a tube) may be inserted into the nose, and then, pressure may be applied to the tube to inject a liquid drug into the nose, like the aforementioned descriptions.

The test device according to the embodiment of the inventive concepts was described above with reference to FIGS. 1 to 3. The test device according to the embodiment of the inventive concepts may naturally induce the nose-to-brain drug inhalation posture, in which the head is directed downward, by the simple operation of seating the unconscious experimental animal on the chair. Thus, the convenience of the operation may be improved. On the contrary, in a typical nose-to-brain drug injection method, an operator may take an experimental animal directly and may inject a drug into a nose of the experimental animal. Thus, a deviation may occur by different skill levels of operators. In addition, even though the same operator performs the drug injection operation, a deviation may occur according to a working environment. However, according to the embodiment of the inventive concepts, the nose-to-brain drug inhalation posture in which the head is directed downward may be naturally induced by the operation of seating the unconscious experimental animal on the chair, and thus the nose-to-brain drug injection may be effectively performed regardless of a skill level of an operator and/or a working environment.

In addition, the test device according to the embodiment of the inventive concepts may include the warm pad disposed at a surface on which the experimental animal is seated, and thus the body temperature of the experimental animal may be maintained to improve a survival rate of the experimental animal. In particular, since the bottom of the chair of the test device is opened, the experimental animal may be seated directly on the warm pad to improve heat transfer efficiency.

Moreover, the test device according to the embodiment of the inventive concepts may induce the mecca position by seating the experimental animal on the chair, and thus a structure of the test device may be simple. Furthermore, the supporter 110 may be configured to vertically move in the height direction and/or to rotate on the x-axis, and thus the working environment with improved convenience may be provided.

Hereinafter, a test method using the test device according to the embodiment of the inventive concepts will be described with reference to FIG. 4.

FIG. 4 is a flowchart illustrating a test method according to an embodiment of the inventive concepts.

Referring to FIG. 4, a test method according to an embodiment of the inventive concepts may include inducing an experimental animal to be in a drug inhalation posture in which the experimental animal is seated on a supporter and is fixed in a state where a head thereof is directed downward (S100), and injecting a drug to a brain of the experimental animal through a nose of the experimental animal induced in the drug inhalation posture (S110). Hereinafter, each of the operations will be described in detail.

In the operation S100, the drug inhalation posture of the experimental animal may be induced. To achieve this, the experimental animal in an unconscious state may be prepared. For example, the unconscious experimental animal may be in an anesthetic state. The unconscious experimental animal may be seated on the chair 130 according to the embodiment of the inventive concepts. Before seating the unconscious experimental animal, the supporter 110 may be moved in the y-axis direction and/or be rotated on the x-axis for work convenience of an operator. After seating the experimental animal on the chair 130, the front of the experimental animal may be fixed by the belt 140. Thus, the experimental animal may take the mecca position in which the head is directed downward, as described with reference to FIG. 3.

In the operation S110, the drug may be injected into the experimental animal induced in the drug inhalation posture. For example, the drug may be a drug which is not supplied to other internal organs through the nose but is selectively supplied to the brain through the nose. An operator may provide the drug to the nose of the experimental animal induced in the mecca position by using the drug injector 190 of FIG. 1 (e.g., a spray-type drug injector). The experimental animal may inhale the drug provided to the nose during a breath, and thus the drug may be injected from the entrance 191 (see FIG. 2) of the nose to the brain 192 (see FIG. 2).

According to an embodiment, the test method may further include maintaining a body temperature of the experimental animal into which the drug is injected. In more detail, the body temperature of the experimental animal may be maintained by the warm pad 120. Thus, it is possible to reduce the risk of death of the experimental animal when waking up the unconscious experimental animal.

The test method according to the embodiment of the inventive concepts was described above.

Hereinafter, test results of nose-to-brain drug delivery of the test device according to the embodiment of the inventive concepts will be described with reference to FIGS. 5 and 6. FIGS. 5 and 6 show test results of nose-to-brain drug delivery of a test device according to an embodiment of the inventive concepts.

To check nose-to-brain drug delivery through the test device according to the embodiment of the inventive concepts, a fluorescent substance was provided to markers to be bonded to acetylcholine (Ach) receptors shown in brain tissue in a rat animal model, and then, the markers provided with the fluorescent substance were delivered through the nose. Thereafter, delivery of the markers to the brain tissue was checked.

In test results shown in FIG. 5, a fluorescent substance Cy5 was provided to RVG peptide and RV-MAT (scrambled peptide) used as the markers, and then, RVG peptide and RV-MAT provided with the fluorescent substance Cy5 were delivered through the nose. After 48 hours, delivery to brain tissue was checked. As a result, both RVG peptide and RV-MAT (scrambled peptide) were delivered to the brain. In addition, RVG peptide was delivered to the whole of the brain tissue by its bonding strength with the Ach receptors. However, RV-MAT corresponding to a control group was mainly bonded to a cortex of the brain tissue and was not delivered to the whole (thalamus, cerebellum and brain stem) of the brain tissue.

In test results shown in FIG. 6, a fluorescent substance SiCy5 was provided to RV-MAT (scrambled peptide) and RVG9R3LC used as the markers, and then, RV-MAT and RVG9R3LC provided with the fluorescent substance SiCy5 were delivered through the nose. After 12 hours, delivery to brain tissue was checked. As a result, both RV-MAT and RVG9R3LC were delivered to the brain but were not delivered to other internal organs.

In other words, according to the test device and the test method of the embodiments of the inventive concepts, the nose-to-brain drug delivery may be effectively performed and the drug may be delivered to a selected region of the brain. In addition, it is possible to inhibit or prevent the drug from being delivered to other internal organs.

The effects of the test device and the test method according to the embodiments of the inventive concepts for inducing the mecca position were described above.

Hereinafter, nose-to-brain drug delivery through the mecca position according to the embodiment of the inventive concepts will be compared with nose-to-brain drug delivery through a non-mecca position. FIGS. 7 and 8 show test results of nose-to-brain drug delivery according to drug injection through a non-mecca position and drug injection through a mecca position according to an embodiment of the inventive concepts.

In the test results illustrated in FIGS. 7 and 8, $Alexa^{488}$, RVG peptide labeled with $Alexa^{488}$, and RV-MAT labeled with $Alexa^{488}$ were used as the markers.

In addition, a sleeping (i.e., unconscious) experimental animal in a non-mecca position, a non-sleeping experimental animal in the non-mecca position, and a sleeping experimental animal in the mecca position were prepared to check effects of the nose-to-brain drug delivery in the mecca position. In FIGS. 7 and 8, the sleeping experimental animal in the non-mecca position is represented as 'Sleeping', the non-sleeping experimental animal in the non-mecca position is represented as 'Awake', and the sleeping experimental animal in the mecca position is represented as 'Mecca'.

In the present test, $Alexa^{488}$, RVG peptide labeled with $Alexa^{488}$, and RV-MAT labeled with $Alexa^{488}$ used as the markers were injected into the experimental animals in the Sleeping state, the Awake state and the Mecca state through their noses.

As a result, in other internal organs, there was substantially no difference in the injection degree of the drug depending on the posture of the experimental animal. However, the drug was injected to the brain of the experimental animal of the mecca position (fluorescence expression: white color), but the drugs were not injected to the brains of the experimental animals of the non-mecca positions.

In other words, it may be recognized that the mecca position is a substantially unique posture capable of performing the nose-to-brain drug delivery. Thus, the test device and the test method according to the embodiments of the inventive concepts may be necessary for the nose-to-brain drug delivery. In addition, the test device according to the embodiments of the inventive concepts may naturally induce the mecca position of the experimental animal, as described above. Thus, differences between test results obtained by different operators may be minimized, and convenience and ease in the nose-to-brain drug delivery test may be improved.

The test device and the test method according to the embodiments of the inventive concepts may be used in various animal research fields.

The test device according to the embodiments of the inventive concepts may include the supporter providing a seating surface for an experimental animal, and the chair formed on the supporter and configured to induce the drug inhalation posture in which a head of the experimental animal is directed downward. Thus, the mecca position may be induced by the simple operation.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A test device comprising:
   a supporter providing a seating surface for an experimental animal; and
   a chair formed on the supporter and configured to induce a drug inhalation posture in which a head of the experimental animal is directed downward,
   wherein a drug is injected to a brain of the experimental animal through a nose of the experimental animal induced in the drug inhalation posture, and
   wherein the supporter extends in a longitudinal direction and the chair is provided in plurality in the longitudinal direction.

2. The test device of claim 1, wherein a warm pad is formed on the supporter, and the warm pad is configured to maintain a body temperature of the experimental animal.

3. The test device of claim 2, wherein a bottom of the chair is opened, and the warm pad is exposed through the chair.

4. The test device of claim 1, wherein the chair comprises: a belt connected to both sides of the chair and configured to fix the experimental animal.

5. The test device of claim 4, wherein the chair surrounds a left side, a right side and a back side of the experimental animal, and the belt surrounds and fixes a front side of the experimental animal.

6. The test device of claim 1, wherein the supporter is configured to rotate on an axis parallel to the longitudinal direction.

7. The test device of claim 1, further comprising: holders disposed at both sides of the supporter to support the supporter, wherein the supporter is vertically movable in a height direction of the holders.

8. A test method comprising:
   inducing an experimental animal to be in a drug inhalation posture in which the experimental animal is seated on a supporter and is fixed in a state where a head thereof is directed downward; and
   injecting a drug to a brain of the experimental animal through a nose of the experimental animal induced in the drug inhalation posture.

9. The test method of claim 8, further comprising:
   maintaining a body temperature of the experimental animal to which the drug is injected.

* * * * *